United States Patent
Moyne et al.

(12) 
(10) Patent No.: US 6,183,736 B1
(45) Date of Patent: Feb. 6, 2001

(54) SMALL PEPTIDES WITH ANTIPATHOGENIC ACTIVITY, TREATED PLANTS AND METHODS FOR TREATING SAME

(75) Inventors: Anne-Laure Moyne, Auburn, AL (US); Thomas E. Cleveland, Mandeville, LA (US); Sadik Tuzun, Auburn, AL (US)

(73) Assignees: USDA/ARS Southern Regional Research Center, New Orleans, LA (US); Auburn University, Auburn University, AL (US)

( * ) Notice: Under 35 U.S.C. 154(b), the term of this patent shall be extended for 0 days.

(21) Appl. No.: 09/287,515

(22) Filed: Apr. 7, 1999

Related U.S. Application Data (60) Provisional application No. 60/080,879, filed on Apr. 7, 1998, and provisional application No. 60/087,535, filed on Jun. 1, 1998.

(51) Int. Cl.[7] .......................... A01N 63/00; A01N 25/00; C12N 1/00; C12N 1/20; C12N 17/00
(52) U.S. Cl. .................. 424/93.462; 424/405; 424/406; 435/71.1; 435/170; 435/252.5; 435/267; 435/839
(58) Field of Search .................................. 435/71.1, 71.3, 435/169, 170, 171, 405, 252.5, 267, 839; 424/93.462, 405, 406, 832

(56) References Cited

U.S. PATENT DOCUMENTS

| | | | |
|---|---|---|---|
| 5,589,381 | * | 12/1996 | Neyra et al. ....................... 435/252.5 |
| 5,662,898 | * | 9/1997 | Ligon et al. ......................... 424/93.2 |
| 5,665,354 | * | 9/1997 | Neyra et al. .......................... 435/115 |

OTHER PUBLICATIONS

Francoise Peypoux et al., "Structures of Bacillomycin D and Bacillomycin L Peptidolipid Antibiotics From Bacillus Subtilis", The Journal of Antibiotics, Dec. 1984, vol. No. 12 (pp1600–1604).

Dirk Konz et al., "Molecular and Biochemical Characterization of the Protein Template Controlling Biosynthesis of the Lipopeptide Lichenysin", Journal of Bacteriology, Jan. 1999, p 133–140.

Sung–Chyr Lin et al., "Structural and Immunological Characterization of a Biosurfactant Produced by Bacillus licheniformis JF–2", Applied and Environmental Microbiology, Jan. 1994, p 31–38.

Michail M. Yakimov et al., "Characterization of a New Lipopeptide Surfactant Produced by Thermotolerant and Halotolerant Subsurface Bacillus licheniformis BAS50", Applied and Environmental Microbiology, May 1995, p 1706–1713.

* cited by examiner

Primary Examiner—Leon B. Lankford, Jr.
Assistant Examiner—Deborah K. Ware
(74) Attorney, Agent, or Firm—Schnader Harrison Segal & Lewis LLP (57) ABSTRACT

The invention relates to two lipopeptides a1 and a2 produced by Bacillus subtilis and their use as an anitfungal agent against Aspergillus flavus. Both peptides are cyclic, acidic and have broad range of antifungal and antimicrobial activity. Both peptides belong to the Bacillomycin D family. A method and composition for controlling aflatoxin contamination in plants susceptible to alflatoxin-producing fungi, like Aspergillus flavus or Aspergillus parasiticus is also disclosed.

29 Claims, 8 Drawing Sheets

SMALL PEPTIDES WITH ANTIPATHOGENIC ACTIVITY, TREATED PLANTS AND METHODS FOR TREATING SAME

RELATED CASES

This application is based on patent applications Ser. No. 60/080,879, filed Apr. 7, 1998, entitled: "Antifungal Peptide", PROV and Ser. No. 60/087,535, filed Jun. 1, 1998, entitled: "Purification of a Small Peptide with Antifungal Activity Against *Aspergillus Flavus*", PROV. This application claims the benefit of the filing dates of both of the above-identified patent applications, which are incorporated herein by reference in their entirety.

STATEMENT REGARDING FEDERALLY SUPPORTED RESEARCH

This invention was made with a U.S. federally supported grant USDA-58-6435-3-122 awarded by the United States Department of Agriculture. The government has certain rights in the invention.

BACKGROUND OF THE INVENTION

1. Field of the Invention

The present invention relates to the control of pathogenic microorganisms, particularly pathogenic fungi and certain bacteria. The invention also relates to lipopeptides having such antipathogenic activity i.e. high antifungal particularly against the Aspergillus genus and antibacterial activity. The invention also relates to the plants which have been treated with the lipopeptides or the microorganisms that synthesize and produce the lipopeptides. The invention also relates to other aspects further described herein.

An important objective of the invention is to address and to contribute to solve the aflatoxin problem that is caused by the aflatoxin-producing fungi, *Aspergillus flavus* and *Aspergillus parasiticus*.

2. Description of the Related Art

Bacillus ssp is known to produce a variety of peptide antibiotics that are antibacterial and/or antifungal. Although the peptides antibiotics are composed of amino acids, they often differed from gene-encoded polypeptides in their structure and mechanism of biosynthesis. Some are gene-encoded and synthesized ribosomally, but these often undergo posttranslational processing and modifications. Antibiotics produced non ribosomally are composed of 2 to 20 amino acids organized in a linear, cyclic or branched cyclic structure. *Bacillus subtilis* produced gene-encoded antibiotics and a variety of small antibiotic peptides with a molecular weight less than 2000 daltons, synthesized non-ribosomally. Subtilin is one gene-encoded lantibiotic peptide synthesized by *B. subtilis* as a prepropeptide that undergoes posttranslational processing (1). Among the antibiotics synthesized non ribosomally are two family: the lipopeptides including iturin, surfactin, fengycin, plistatin and the small hydrophilic di- and tripeptides. Iturin is a group of cyclic lipopeptides produced by *Bacillus subtilis* including iturin A, C, D and E (2,3), bacillomycin D, F and L (4), Bacillopeptin (5) and mycosubtlin (6). All contains a β-amino fatty acid linked by amide bonds to the constituent amino acid residues of the iturin group. Iturin lipopeptide share a common sequence [β-hydroxy fatty acid-Asx-Tyr-Asx] and show variation at the other four positions. Surfactin is also a cyclic lipopeptide containing seven residues of D- and L-amino acids and one residue of a β-hydroxy fatty acid (7) with an amino acid sequence completely different from the iturin group. It is a powerful surfactant and has been described as an antifungal agent. Fengycin (8) and plipastatin (9) are lipopeptide with ten amino acid and a lipid attached to the N-terminal end of the molecule. They differed from iturin and surfactin by the presence of unusual amino acid such as ornithine and allo-threonine.

Table 1 shows the amino acid residues of the iturins and the chemical structure of Bacillomycin D.

TABLE I

| Antibiotic | Amino acid residues | | | | | | | Major β amino acid |
|---|---|---|---|---|---|---|---|---|
| | L | D | D | L | L | D | L | |
| Iturin A | Asn | Tyr | Asn | Gln | Pro | Asn | Ser | $n\text{-}C_{14}$, $i\text{-}C_{15}$, $a\text{-}C_{15}$ |
| Iturin C | Asp | Tyr | Asn | Gln | Pro | Asn | Ser | $n\text{-}C_{14}$, $i\text{-}C_{15}$, $a\text{-}C_{15}$ |
| Bacillopeptin | Asn | Tyr | Asn | Ser | Glu | Ser | Thr | $n\text{-}C_{14}$, $i\text{-}C_{15}$, $i\text{-}C_{16}$ |
| Bacillomycin D | Asn | Tyr | Asn | Pro | Glu | Ser | Thr | $n\text{-}C_{14}$, $i\text{-}C_{15}$, $a\text{-}C_{15}$ |
| Bacillomycin F | Asn | Tyr | Asn | Gln | Pro | Asn | Thr | $i\text{-}C_{16}$, $i\text{-}C_{17}$, $a\text{-}C_{17}$ |
| Bacillomycin L | Asp | Tyr | Asn | Ser | Gln | Ser | Thr | $n\text{-}C_{14}$, $i\text{-}C_{15}$, $a\text{-}C_{15}$ |
| Mycosubtilin | Asn | Tyr | Asn | Gln | Pro | Ser | Asn | $i\text{-}C_{16}$, $a\text{-}C_{17}$ |

Primary structure of iturins.
Bacillomycin D

C14, C15 or C16 β fatty amino-acid——L-Asn——D-Tyr——L-Asn
                                                                 |                       |
                                              L-Thr——D-Ser——L-Glu——L-Pro Iturin exhibit a restricted antibacterial activity and a broad range of antifungal activity against fungi and yeast but none of them has been shown to have antifungal activity against *A. flavus* although iturin A has already been patented for control of aflatoxin (10). Culture filtrate from *B. subtilis* were described in 1948 as antifungal against important dermatophytes and systemic fungi, and the undescribed antibiotic was named "Bacillomycin" (11). Since then 3 class of bacillomycin D (12), F (13) and L (14), have been characterized according to their amino acid sequence. Among each class, different antibiotics have been reported such as bacillomycin Fa, Fb, Fc, and Lc. Bacillomycin Fb and Fc differ from bacillomycin Fa by the presence of one or two carboxyl group respectively instead of carboxamide groups and bacillomycin Lc from bacillomycin L only by the sequence positions of a side chain amide and a carboxylic acid (15). An exhaustive study of the literature show that bacillomycin F has been tested against a wide range of fungi and bacteria (Table II).

TABLE II

| | MIC (ug/ml) | | |
|---|---|---|---|
| Test Organisms | Bacillomycin Fb | Bacillomycin Fc | Bacillomycin Fa |
| Aspergillus niger | 25 | 30 | 40 |
| Botrytis cinerea | | | 20 |
| Cladosporium cladosporioides | 25 | 40 | |
| Fusarium oxysporum | >200 | >200 | >320 |
| Mycosphaerella pinodes | 100 | 30 | 10 |
| Neurospora crassa | | | 80 |
| Penicillium chysogenum | | | 20 |
| Pleospora herbarum | | | 10 |
| Rhodotorula pillimanae | | | 80 |
| Sclerotina fructigena | | | 40 |
| Sclerotina sclerotiorum | | | 50 |
| Stemphylium radicinum | | | 320 |
| Trichophyton mentagrophytes | | | 20 |
| Candida albicans | >200 | >200 | 40 |
| Candida tropicalis | >200 | >200 | 40 |
| Saccharomyces cerevisiae | 25 | 30 | 10 |
| Azotobacter vinelandii | | | >400 |
| Brucella brochiseptica | | | >400 |
| Escherichia coli K12 | | | >400 |
| Streptomyces albus G | | | >400 |
| Bacillus cereus | | | >400 |
| Micrococcus luteus | | | 200 |
| Sarcinia lutea | | | >400 |
| Staphylococcus aureus | | | >400 |
| Kluyveromyces bulgaris | 75 | 40 | |

Bacillomycin F showed a strong antifungal activity against various yeasts, fungi and phytopathogenic fungi but a weak antibacterial activity (16). Bacillomycin Lc has been described as a new antibiotic of the bacillomycin family with antifungal activity against phytopathogenic fungi such as *Ophiostoma ulmi, Verticillium dahliae, Ceratocystis fagacearum* and *Cryphonectria parasitica* the causal agents of Dutch elm disease, Verticillium wilt of maples, oak wilt and chestnut blight respectively. Bacillomycin D has been reported to be antifungal against *Absydia corymbifera, Aspergillus Niger, Candida Albicans, Fusarium oxysporum, Kluyveromyces bulgaris* and *Saccharomyces cerevisae* (17).

Mycosubtlin, iturin A and bacillomycin L inhibited the growth of *Micrococcus luteus,* their activity are different upon *Micrococcus luteus* protoplast. Mycosubtlin and Iturin A are able to lyse *Micrococcus luteus* protoplast and bacillomycin L has no effect (18). Even a slight modification of the molecule as the methylation of the aspartyl residues of bacillomycin L gives a strong lytic activity while natural bacillomycin L has no lytic activity (19). The phenolic group of the tyrosine residue has been shown to be essential for the antifungal activity, when the tyrosine residue was substituted no activity was observed (20).

Aflatoxin Problem

The invention relates and contributes to solve an important scientific problem of serious economic and business consequences in the United States and in the world. To date, there is no acceptable and effective way and means to control aflatoxin on plants susceptible to aflatoxin-producing fungi. There are no known aflatoxin-resistant plants, genetically transformed or otherwise.

Drought stress and high temperatures at critical times during kernel or seed development and/or insect injury of crops can contribute heavily to aflatoxin contamination of corn by the aflatoxin-producing fungi, *A. flavus* and *A. parasiticus.* The aflatoxin-producing fungi, *A. flavus* and *A. parasiticus,* present health hazards to humans and animals through the toxic and carcinogenic properties of their secondary products. Even a very low level of aflatoxin contamination can lead to severe economic losses in the peanut industry. To control this problem, breeding peanut varieties resistant to Aspergillus sp. or which support less aflatoxin production has been attempted with limited success.

No commercial corn hybrids with high resistance to either infection by *A. flavus* or to aflatoxin accumulation are currently available. Aflatoxin detected at levels of 20 parts per billion (ppb) (established by the FDA) or above can make the crop unsalable. Aflatoxin is considered to be toxic to livestock being fed contaminated grain and to be a carcinogen, correlated with liver cancer, in certain human populations around the world. Cottonseed grown in the Yuma Valley, Ariz., corn grown in certain states of the southern U.S. and peanuts grown in certain regions of Georgia are chronically contaminated with aflatoxins resulting in direct losses by farmers amounting to tens of millions of dollars annually. Corn grown in the mid western states are contaminated with aflatoxin on a sporadic basis. Exact economic losses due to sporadic or limited aflatoxin outbreaks are difficult to determine, particularly in terms of detrimental impact at each of the various steps in the marketplace (including foreign markets). However, during drought years (1983 and 1988) in the mid west corn belt, which led to large aflatoxin outbreaks, losses were estimated to total in the hundreds of millions of dollars.

A major outbreak of aflatoxin in Southern Grown Corn, occurred recently in 1998. Aflatoxin contamination of corn in Arkansas, Georgia, Louisiana, Mississippi, Missouri, South Carolina, Tennessee, and Texas in 1998 was one of the worst ever recorded. A potentially record number of grain-load rejections, due to aflatoxin levels in excess of FDA limits, occurred in some southern states. The aflatoxin outbreak in 1998 has additional significance since corn production in certain southern states has probably tripled in the past three years. It is certainly no coincidence that continuous days of 90(+) F temperatures and low or no rainfall dominated weather conditions for significant portions of the 1998 growing season in Southern states. The literature indicates that these conditions are highly conducive, even necessary for large aflatoxin outbreaks in susceptible crops. Insect injury is often suggested to be the major mode of entry by aflatoxin producing fungi. However, insect injury apparently does not account for the enormity of the aflatoxin outbreak experienced this past year in the South. Thus, controlling insects (e.g. cultivation of transgenic corn containing Bt, an insect toxin), although an essential part of good management practices, would not necessarily have been effective in reducing aflatoxin levels in Southern-grown corn in 1998. Some observations suggest that the fungus gained entry by some other, little understood means associated with high temperature and drought conditions. This highlights the need for extensive research on drought and temperature effects on plant health and physiology and fungal virulence and to find a solution to these problems.

In accordance with the invention, a method, microorganisms of the Bacillus family, peptides synthesized by the Bacillus, especially by *B. subtilis* have been discovered that contribute an important technical advance to the resolution of the aflatoxin problem.

SUMMARY OF THE INVENTION

The invention provides microorganisms of the Bacillus ssp, especially *B. subtilis* preferably *B. subtilis* AU 195 which is effective to control plant pathogens both fungi and bacteria. An important embodiment provides the control of aflatoxin in plants susceptible to aflatoxing-producing fungi. The treatment of the plant can be carried out at anytime, e.g. prior to, or after the onset of the infection. The control can be effectuated with the *B. subtilis* with which synthesizes the antifungal peptides or by the peptides themselves, one at a time or together. Several methods and means of control of aflatoxin producing fungi are provided. Any part of the plant, including the seeds can be treated.

The peptides can be used in a purified form or as crude extract, in aqueous or non-aqueous composition.

Isolation, sequencing and identification of the gene(s) expressing the antifungal peptides, or their functional equivalent, and the transformed plants resistant to aflatoxin-producing fungi, such crops like corn or peanut, susceptible to infection by aflatoxin-producing fungi, is being contemplated.

In particular, the invention provides a family of antifungal peptides, especially two which are of present interest which are antifungal against *A. flavus*.

The present invention provides *B. subtilis*, which shows high antifungal activity against *A. flavus* and also shows antibacterial activity against certain bacteria. The *B. subtilis* strain AU195 produces two small cyclic peptides exhibiting a range of antifungal activity against plant pathogenic fungi. Both peptides have a spectrum of activity against plant fungi and against bacteria heretofore not reported, which make these peptides, very valuable in the control of plant pathogens on plants susceptible to infection caused by pathogens, particularly to aflatoxin-producing fungi like *A. flavus* and *A. parasiticus*.

The invention also related to a method for controlling the diseases of plants caused by such pathogens, and the plants treated with the microorganisms which generates these peptides or with compositions which comprises *B. subtilis*, extracts thereof or the peptides synthesized by the microorganisms.

The invention also related to a *B. subtilis* AU195 has been deposited at the ATCC under Accession number PTA-1767 on Apr. 27, 2000, at the American Type Culture Collection (ATCC), 10801 University Boulevard, Manassas, Va. 20110-2209, and was tested on May 4, 2000 and found to be viable.

DETAILED DESCRIPTION OF THE FIGURES

Figure 1:
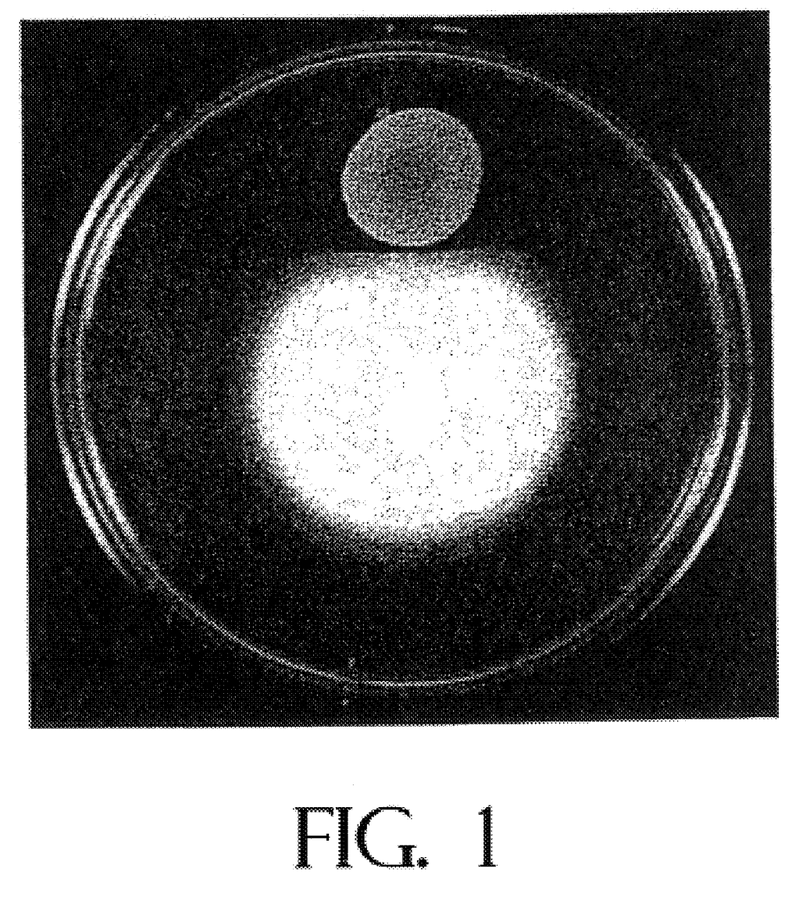
FIG. 1 shows the in vitro inhibitory activity of the strain *B. subtilis* AU195.

FIG. 1 shows the in vitro inhibitory activity of the strain *B. subtilis* AU195.

Figure 2:
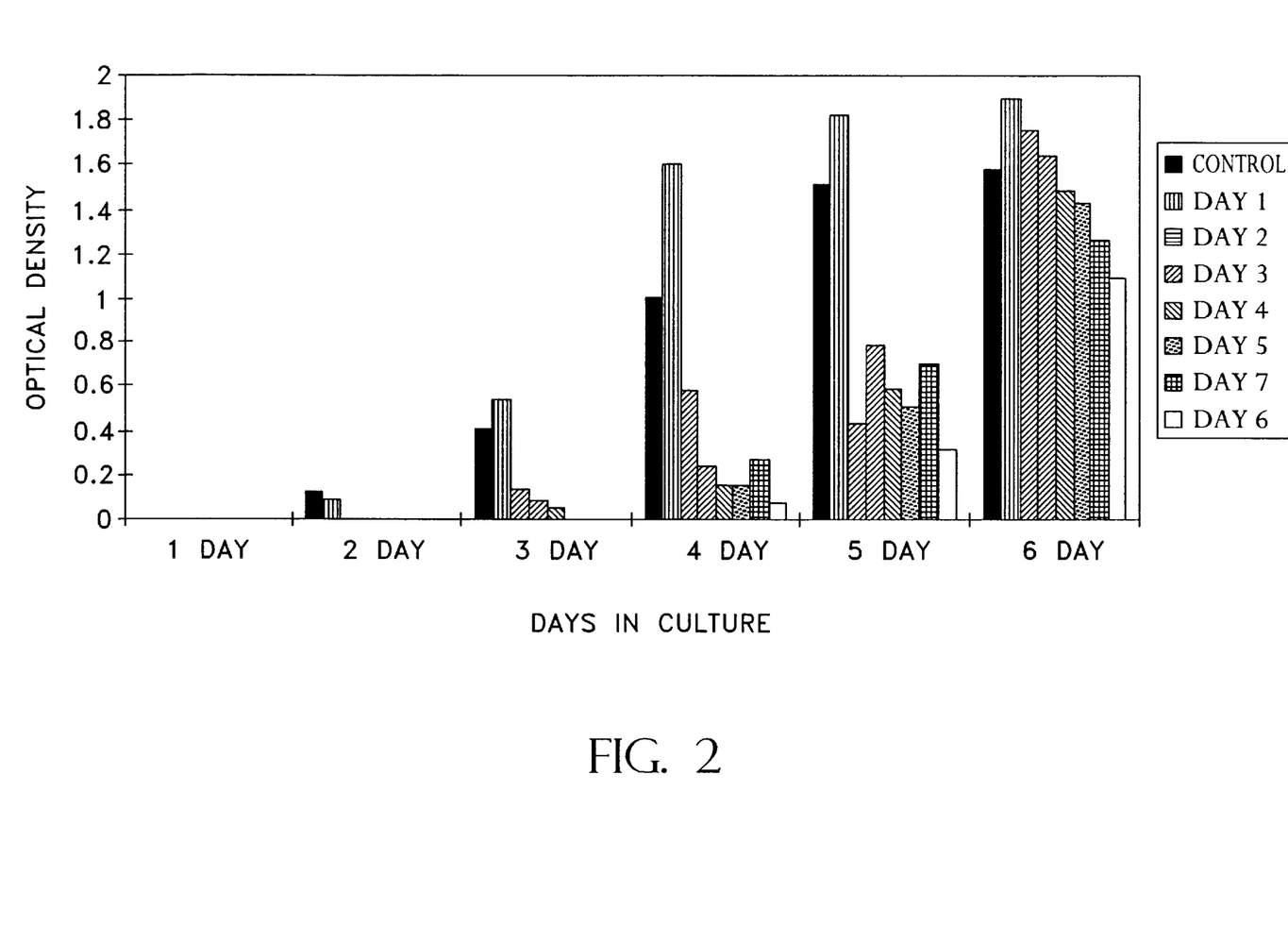
FIG. 2 shows the production of antifungal peptides by *B. subtilis* AU195 and the inhibition of *A. flavus* growth.

FIG. 2 Effect of culture filtrate on growth of *Aspergillus flavus* as measured by absorbency at 560 nm daily during 6-day period. Control sample represents the fungal growth in PDB medium (500 spores/per well in 100 $\mu$l LB and 100 $\mu$l PDB). Other histograms represent the growth of the fungus in the presence of samples from culture filtrate obtained at day 1, day 2, day 3,day 4,day 5, day 6 and day 7 (100 $\mu$l of LB is replaced by 100 $\mu$l of culture filtrate).

Figure 3:
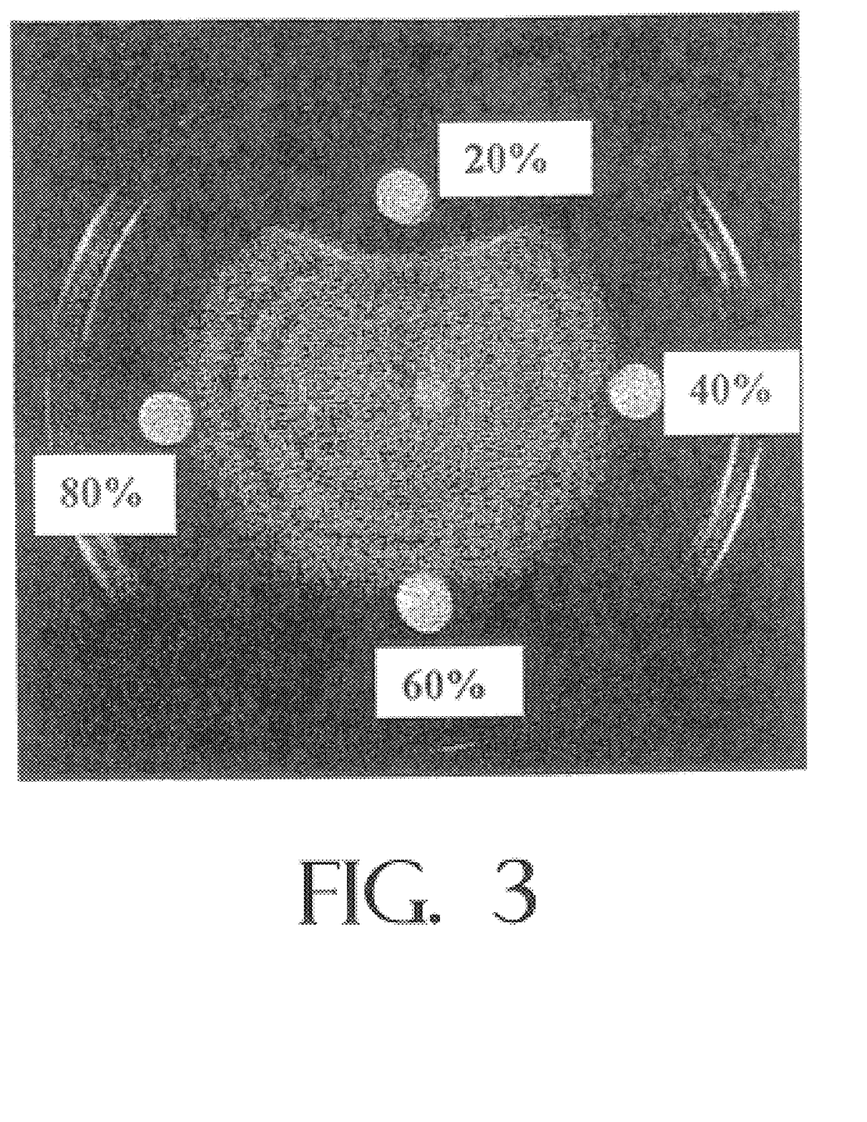
FIG. 3 shows the inhibition of fungal growth by protein fractions.

FIG. 3 Inhibition of fungal growth by protein fraction precipitated with 20, 40, 60 and 80% ammonium sulfate. A mycelial plug of *Aspergillus flavus* was placed on PDA plate 3 days prior to application of samples to allow establishment of the fungus. The samples were placed at an equal distance (5 mm) from the edge of the mycelial growth. 50 $\mu$l of protein sample precipitated with 20–80% ammonium sulfate was placed on a Whatman filter disk.

Figure 4:
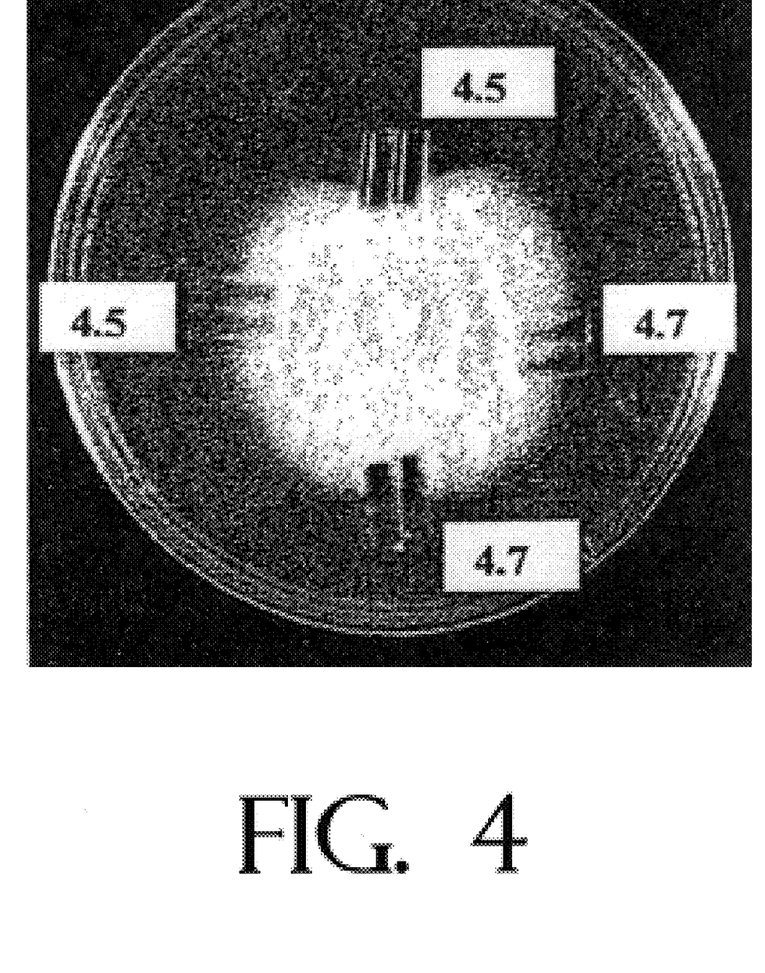
FIG. 4 shows that the antifungal activity is associated with acidic peptides.

FIG. 4 Inhibition of fungal growth by acidic peptides. After IEF electrophoresis, two independent gel segments (with a pH of 4.5 and 4.7, respectively) either containing the sample (top and bottom) or LB as control (left or right) were inoculated with *A. flavus*. This assay clearly demonstrated that the ampholytes are not antifungal and the activity was strictly associated with the a fraction of the gel representing a pH of 4.5.

Figure 5:
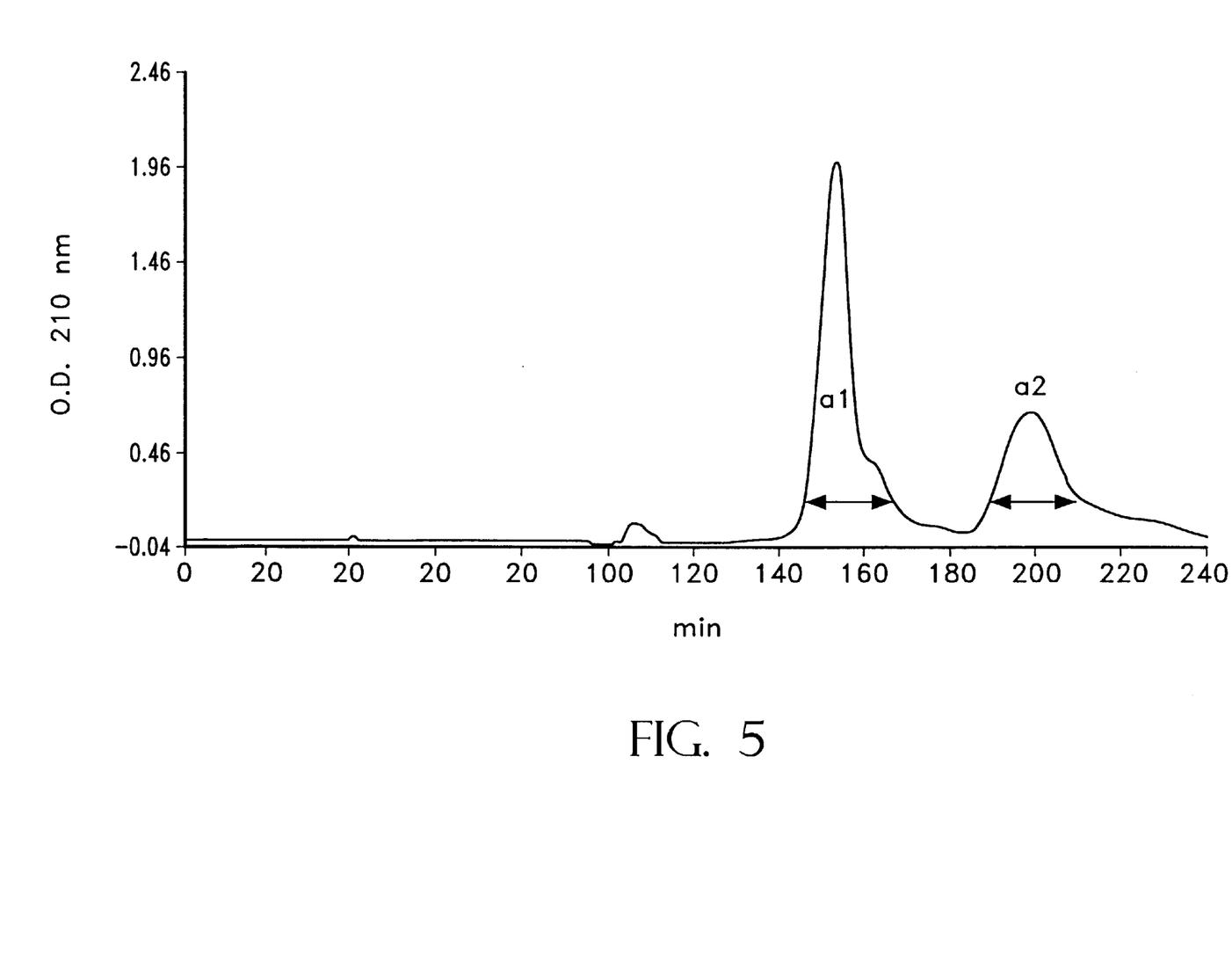
FIG. 5 shows the separation of the antifungal peptides a1 and a2 on superdex peptide Hiload 16/60 column.

FIG. 5 Separation of the antifungal peptides a1 and a2 on superdex peptide Hiload 16/60 column.

Figure 6A:
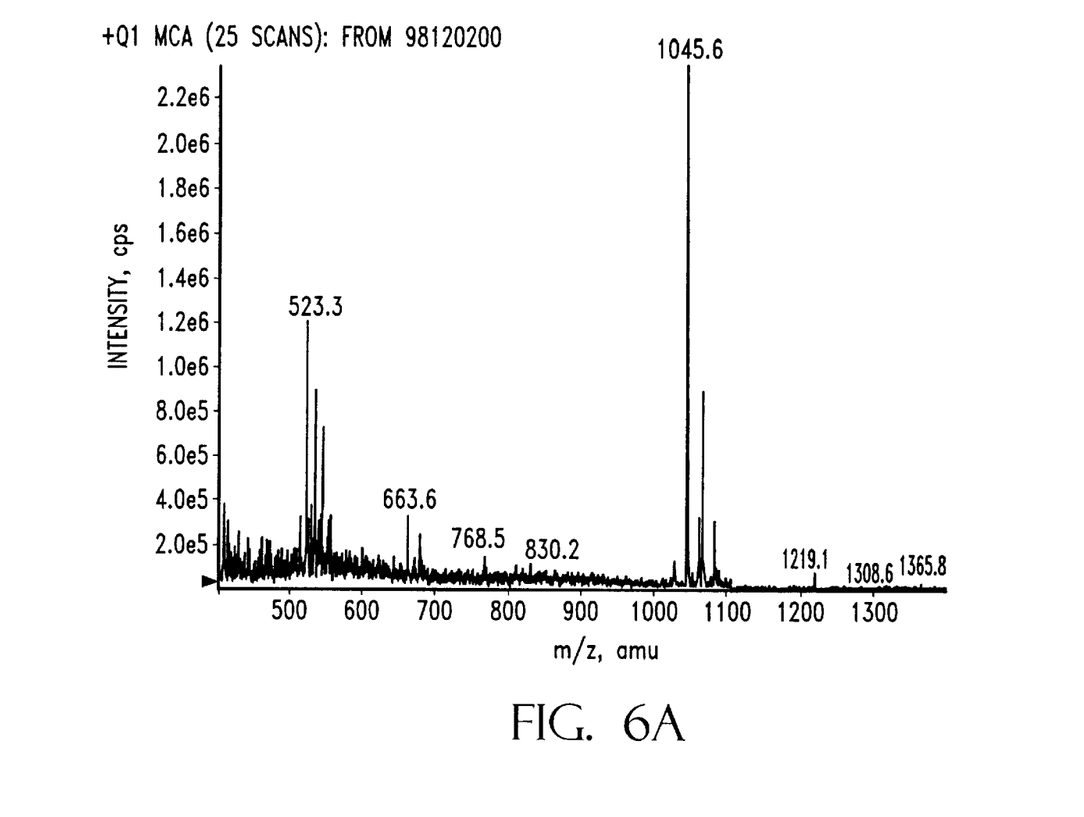
FIG. 6 shows the FAB-MS spectrum of antifungal peptides a1 (a) and a2(b).
Figure 6B:
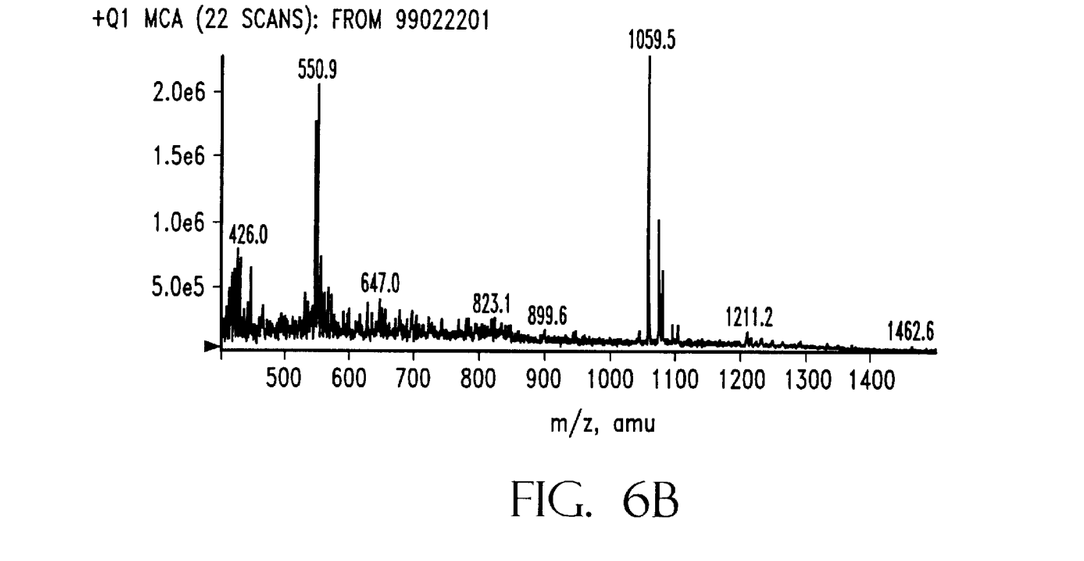

FIG. 6 shows the FAB-MS spectrum of antifungal peptides a1 (a) and a2(b).

Figure 7:
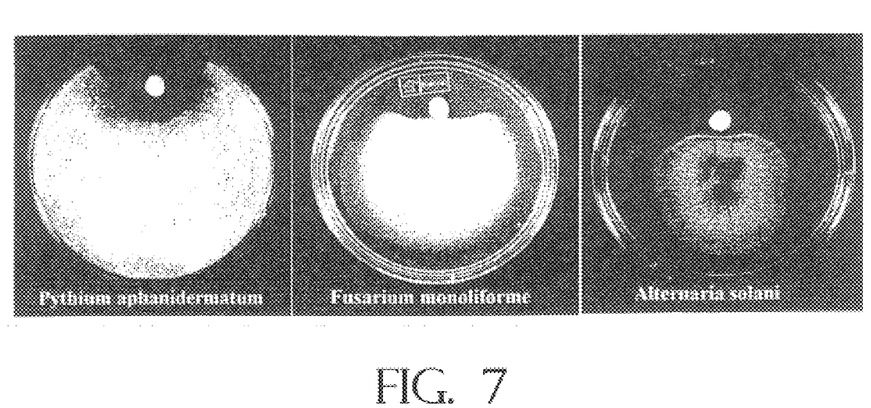
FIG. 7 shows the antifungal activity on three different fungi.

FIG. 7. shows the antifungal activity on three different fungi.

Figure 8A:
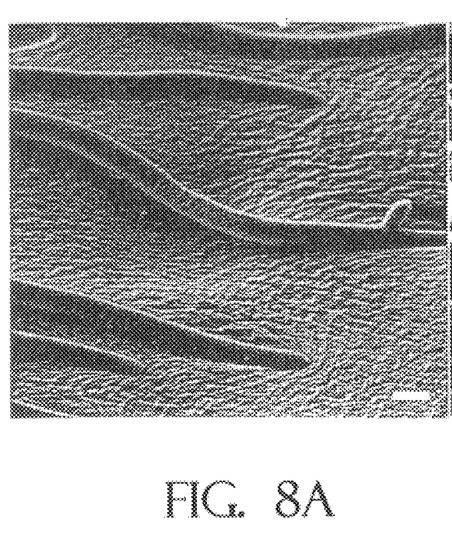
FIG. 8 shows the difference between the normal growth of *A. flavus* (A) and growth of *A. flavus* in the presence of an antifungal extract (B).
Figure 8B:
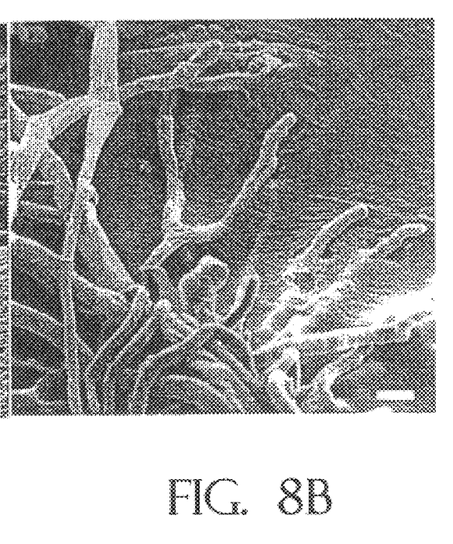

FIG. 8. Pictures represent *A. flavus* growth on PDA plate view with Scanning Electron Microscope (SEM): A) normal hyphae; B) hyphae growing in presence of the antifungal fraction. Bar represent 10 $\mu$m

DETAILED DESCRIPTION OF THE INVENTION

The family of peptides, which have antifungal and antibacterial activity against a spectrum of fungi and bacteria include two small peptides designated herein as a1 and a2. These peptides were found to be associated and isolated from *B. subtilis* AU195. They were characterized as iturin and belong to the bacillomycin D family. Although as has been reported above, bacillomycin D peptides have been found to have antifungal activity, no peptide has been reported to date to have antifungal activity against certain specific fungi, to which plants are susceptible, specifically *Alternaria solani, Fusarium monoliforme, Pythium aphanidermatum*, and especially *A. flavus*.

Other pathogenic fungi to which plants are known to be susceptible include *Puccinia ssp., Phytophthora ssp., Peronospora ssp., Rhizoctonia ssp., Botrytis ssp., Sclerotinia ssp.* and *Colletotrichum ssp*, which can be controlled with the peptides of the invention.

Further, as has been reported, certain peptides which were isolated from bacteria, have been found to have antibacterial activity, which are human pathogens. In contrast, the peptides of the invention have been found to be effective against plant pathogenic bacteria such as, *Xanthomonas campestris* (*X. campestris*) is known to be pathogenic, for instance on cabbage plants and is responsible for black rot disease. Further, the peptides are effective against certain bacteria-like *Clavibacter michiganensis* and *B. cereus*.

The composition of the invention comprises one or more of the principal two peptides discovered namely a1 and a2 in a mixture with conventional biologically acceptable inert or active carriers. The peptides can be used together or administered to the plant, or to the animal sequentially, or only one of the fungal peptides need to be used.

The amount in which the peptide is used in a minimum amount effective to control or inhibit the target fungi or bacteria to a maximum as may be needed for control.

Instead of the isolated peptide, the microorganism, the *B. subtilis* can be used by itself or in the composition, preferably with an appropriate ingredient that promotes the release of the peptide(s). It is not excluded that the spores of *B. subtilis* (e.g. *B. subtilis* AU 195) may be used. These would be allowed to grow on the plant and release the peptides.

The peptides a1 and a2 of the invention have been characterized as described hereafter. They have, respectively, a 1045 Da and 1059.5 ba molecular weight, determined by mass spectroscopy. It is believed that a1 has a β-amino fatty acid of 15 carbons and that a2 has a β-amino fatty acid of 16 carbons. The tandem mass spectrometry of a2 indicated a sequence very similar to a1 with an additional $CH_2$ at some point other than the Glu residue. It is not excluded that the length of these amino acids vary each by 1–3 carbons, i.e., be shorter or longer accordingly. The mass shift of a2 may be accountable by a homoserine for the serine residue or a fatty acid modifier one carbon longer than a1 or a single amino acid substitution of some type.

The target plant or mammal, which can be treated is any plant susceptible to the fungal or microbial infection to be controlled, like the major crops, whether monocotyledonous or dicotyledonous, like cereals, legumes, tubers, solanaceous plants, cucurbits, fibrous plants, corn, peanut, rice, wheat, etc. Of particular interest at this time in the treatment of peanut plants which are susceptible to aflatoxin-producing fungi. Peanut plants including the seeds can be treated in accordance with the invention.

Any mammal especially animals susceptible to *A. flavus* or and/or *A. parasitus* can also be treated with the compositions including the peptides of the invention.

The peptides of the inventions are generally obtained as a mixture of isomers in a mixture with other peptides that do not interfere with the activity of the peptides of the invention. The isomeric mixture can be separated into the respective isomers by know inventions.

Upon isolation and sequencing of the gene(s) which codes the peptides of the invention, the plants like corn, soybeans, peanut and other crops can be readily transformed (either by nucleus or chloroplast transformation) to produce plants resistant to the target infection, and likewise produce progeny (and maternally inherited) generations, that are likewise stably resistant to the target pathogen(s).

Any mammal, especially animals susceptible to *A. flavus* and/or *A. parasiticus* can be treated on accordance with the invention.

The peptides can be used for prophylactic control and/or therapeutic control.

Other embodiments of the invention will become apparent from the description herein.

The following Examples are not intended to limit the invention in any manner whatsoever, they are purely illustrative.

EXAMPLE 1

Description of the producing strain (see Table III). Table III gave the identification of the AU 195 as a *Bacillus subtilis* strain with gas chromatography of fatty acid methyl ester. AU195 produces a pigment, which gave an orange color to the culture filtrate. FIG. 1 shows the in vitro inhibitory activity of the strain *B. subtilis* AU195.

TABLE III

| RT | Area | Ar/Ht | Respon | ECL | Name | % | Comment 1 | | Comment 2 | |
|---|---|---|---|---|---|---|---|---|---|---|
| 0.311 | 450 | 0.036 | ... | 4.365 | .......... | ... | < min rt | | | |
| 1.457 | 360188400 | 0.049 | ... | 7.041 | SOLVENT PEAK .... | ... | < min rt | | | |
| 5.923 | 618 | 0.039 | 1.002 | 13.617 | 14:0 ISO ...... | 0.90 | ECL deviates | −0.001 | Reference | −0.005 |
| 7.295 | 19890 | 0.033 | 0.971 | 14.622 | 15:0 ISO ...... | 28.09 | ECL deviates | 0.001 | Reference | 0.000 |
| 7.423 | 27120 | 0.034 | 0.968 | 14.712 | 15:0 ANTEISO .... | 38.20 | ECL deviates | 0.001 | Reference | −0.001 |
| 8.818 | 1476 | 0.049 | 0.946 | 15.624 | 16:0 ISO ...... | 2.03 | ECL deviates | −0.002 | Reference | −0.003 |
| 9.024 | 1158 | 0.042 | 0.943 | 15.755 | 16:1 w11c ..... | 1.59 | ECL deviates | −0.002 | | |
| 9.409 | 1938 | 0.036 | 0.938 | 16.000 | 16:0 ........ | 2.65 | ECL deviates | 0.000 | Reference | −0.001 |
| 10.045 | 2058 | 0.039 | 0.932 | 16.384 | ISO 17:1 w10c ... | 2.79 | ECL deviates | −0.003 | | |
| 10.195 | 1014 | 0.047 | 0.930 | 16.474 | Sum In Feature 5 .. | 1.37 | ECL deviates | −0.002 | 17:1 ISO I/ANTEI B | |
| 10.453 | 8904 | 0.040 | 0.928 | 16.630 | 17:0 ISO ...... | 12.02 | ECL deviates | 0.001 | Reference | −0.001 |
| 10.605 | 7692 | 0.040 | 0.927 | 16.722 | 17:0 ANTEISO .... | 10.37 | ECL deviates | −0.000 | Reference | −0.002 |
| 19.443 | 846 | 0.186 | ... | 21.927 | .......... | | > max rt | | | |
| ******* | 1014 | ... | ... | ... | SUMMED FEATURE 5 .. | 1.37 | 17:1 ISO I/ANTEI B | | 17:1 ANTEISO B/i I | |

| Solvent Ar | Total Area | Named Area | % Named | Total Amnt | Nbr Ref | ECL Deviation | Ref ECL Shift |
|---|---|---|---|---|---|---|---|
| 360188400 | 71868 | 71868 | 100.00 | 68741 | 7 | 0.002 | 0.002 |

| | |
|---|---|
| TSBA [Rev 3.80] Bacillus ..................... | 0.904 |
| *B. subtilis* .................. | 0.904 |
| *B. amyloliquefaciens* .............. | 0.553 (*Bacillus subtilis* group) |
| CLIN [Rev 3.80] Bacillus ..................... | 0.569 |
| *B. subtilis* .................. | 0.569 |

EXAMPLE 2

Description of the method for the antifungal assays. Microtiter plate assay: Samples were tested for their antifungal activity against *Aspergillus flavus* in a microtiter plate (Falcon 3918, Becton-Dickinson and Company). Each well contained 100 μl Potato Dextrose Agar (PDA, Difco Laboratories) and 100 μl of sample and was inoculated with 500 spores of *Aspergillus flavus*. Fungal growth was monitored by reading optical density (O.D.) at 560 nm (Dynatech microplate reader).

Disc plate diffusion assay : Antifungal activity of the different purification steps were carried out under sterile conditions using the disc plate diffusion assay. Mycelium plugs from actively growing fungal cultures were placed in the center of the petri plate. After incubation at 27° C. to allow vegetative growth, samples were applied on sterile filter paper discs laid on the agar surface.

EXAMPLE 3

Production of the antifungal peptides. AU195 has been cultured in LB medium and culture filtrate was sampled daily. Samples were filter sterilized and incubated in presence of *Aspergillus flavus* spores in microtiter plates which enabled us to measure fungal growth spectrophotometrically as described in example 2. The antifungal peptides secreted into the culture filtrate by AU195 increased every day (FIG. 2).

EXAMPLE 4

Temperature stability and sensitivity to enzyme. 7-day culture filtrate was boiled for 20 minutes and then tested for antifungal activity. 50 $\mu$l of 7-day culture filtrate were incubated with 200 $\mu$g of lipase from wheat germ (sigma) in 50 mM tris HCl pH 7.5. Incubation with enzymes was carried out at 37° C. for 2 hours. The activity of the samples was then tested with a disc diffusion assay as described in example 2 and compared with that of a control.

There was no decrease in the antifungal activity when the 7-day culture filtrate is boiled, kept at room temperature for 7 days or one month or incubated with lipase. This indicated that the peptides are very stable.

EXAMPLE 5

Solubility. 7-day culture filtrate was freeze-dried and resupended in methanol, ethanol, butanol, ether, chloroform and acetone. Solvent was removed by evaporation, samples were dissolved in water and tested using the disc filter assay described in example 2.

The antifungal peptides were soluble in water, methanol, ethanol, butanol and insoluble in ether, chloroform and acetone. Solubility in polar solvent indicated that they are hydrophilic.

EXAMPLE 6

Precipitation with ammonium sulfate. The 7$^{th}$ day culture filtrate was sequentially precipitated with 20, 40, 60 and 80% ammonium sulfate. Using a disk filter assay as described in example 2, only fraction precipitated with 20% ammonium sulfate exhibited antifungal activity against Aspergillus flavus (FIG. 3).

EXAMPLE 7

PI of the antifungal peptides. To characterize the antifungal peptides, the fraction precipitated with 20% ammonium sulfate was further separated with isoelectro focusing (IEF) tube gel electrophoresis. For this purpose, 1 mg of protein sample was loaded on a tube gel containing ampholytes (pH 2–8) and after electrophoresis gels were cut in 1 cm pieces. Each piece (total of 15) was placed on an agar media that was already inoculated with the fungus. FIG. 4 represents the result of an antifungal assay against *Aspergillus flavus* after separation of the Bacillus proteins depending on their pI.

EXAMPLE 8

Purification of the antifungal peptides. Bacterial cells were removed by centrifugation after 7 days of culture and proteins were precipitated with ammonium sulfate. After centrifugation, the pellet was dialyzed against water, acidified to pH 3 with 12N HCl and centrifuged. After resuspending in water and adjusting pH to 7, pellet was loaded on a 5 ml anion exchange column (HiTrap Q pharmacia). The column was connected to an FPLC system (ConSep LC 100, PerSeptive Biosystems) and a linear gradient of 0 to 1.6M NaCl including 20 mM phosphate buffer pH 7 was applied. 5 ml fractions were collected, tested for antifungal activity using a filter disk assay as described in example 2 and dialyzed against water. All the fractions with antifungal activity were pooled together and loaded on a preparative superdex peptide hi load 16/60 column (Pharmacia). The antifungal fractions were separated twice on this column until the antifungal peaks were fully separated (FIG. 5).

EXAMPLE 9

Molecular weight of both antifungal peptides. The molecular weights of both peptides were determined by FAB mass-spectrophometry. The spectra for the antifungal peptide a1 indicated a mass [M+H] of 1045.5 and for the antifungal peptide a2 1059.5 (FIG. 6).

EXAMPLE 10

Amino Acid sequence of A1 and A2. Initial Edman sequencing was unsuccessful and tandem mass spectrometry of the molecular ion resulted in a highly complex spectrum which suggested a cyclic structure for both peptides.

A1 was digested to give a linear molecule and the sequence after digestion at the Glu—C amino acid was: NH2- STNYNPE-OH. A modification of the molecule at the Thr residue suggested the attachment of hydroxy fatty acid. A1 has the same amino acid sequence and mass than one of the bacillomycin D (21).

Tandem mass spectrometry of the cyclic form of A2 indicated a sequence very similar to A1 with an additional CH2. A2 has an amino acid sequence similar to bacillomycin D but its mass is higher m/z 1059.5 than the one published by Peypoux et al. (20) (m/z 1031 and 1045).

EXAMPLE 11

Antifungal activity of the crude fraction. The crude fraction included all the protein secreted in the culture filtrate of *B. subtilis* AU195 culture and precipitated with 20% ammonium sulfate. Both antifungal peptide a1 and a2 were present in the crude fraction in a mixture of 50/50. Antifungal activity of fraction obtained after ammonium sulfate precipitation was carried out under sterile conditions using the disc plate diffusion assay described in example 2. Mycelium plugs from actively growing cultures were placed in the center of a petri plate containing PDA for *Alternaria solani, Fusarium monoliforme* and *Pythium aphanidermatum*. After incubation at 27° C. to allow vegetative growth, samples were applied on sterile filter paper disc laid on the agar surface. The crude fraction is able to inhibit hyphal growth of *Alternaria solani, Fusarium monoliforme* and *Pythium aphanidermatum* (FIG. 7).

EXAMPLE 12

Antifungal activity of the purified peptides. After complete purification of the antifungal peptides as described in example 8, removing salt by purification on a Sepack cartridge (waters) and freeze drying, both peptides were quantified by weight. Table IV shows the result of the antifungal assay. The antifungal assays are described in example 2.

TABLE IV

|  | Disc plate diffusion assay Minimal amount to inhibit hyphal growth | Microtiter plate Minimal inhibitory concentration (MIC) |
| --- | --- | --- |
| Iturin A | No inhibition with 50 μg | 250 μM |
| a1 | 15 μg | Not tested |
| a2 | 3 μg | 130 μM |

In a similar manner the purified peptides each one individually or in a mixture (40/60) control the growth of *A. parasiticus*.

When peanut plants are treated with the compositions of Examples 11 and 12, the plants are expected to show improved resistance to *A. flavus*. Similarly improved resistance to *A. flavus* is expected by corn plants.

EXAMPLE 13

Antimicrobial activity of the crude fraction 3 or 5 ml of bacterial cell suspension (from $10^4$ to $10^8$ cells/ml) was widespread at the surface of LB plate and the excess was withdrawn. After 15 min dessication of plates under the hood, 4 discs were distributed containing different amount of the ammonium sulfate precipitate fraction. Plates were incubated for 48 hours at 27° C. and the inhibition zone was observed after 24 and 48 hours. Results are given in Table V for all the strains tested.

TABLE V

| Bacteria tested | Antimicrobial activity of the ammonium sulfate precipitated fraction |
| --- | --- |
| Escherichia coli | − |
| Clavibacter michiganensis | ++ |
| Pseudomonas fluorescens | − |
| Xanthomonas campestris | + |
| Erwinia carotovora | − |
| Bacillus subtilis AU195 | ++ |
| Bacillus cereus | ++ |

−, no inhibition;
+, poor inhibition;
++, good inhibition

All publications referenced herein are hereby incorporated by reference in their entirety. The invention is not limited to the embodiments described herein, but encompasses modifications with the scope of the following claims and equivalent thereof.

REFERENCES

1. Nishio C., Komura S. and Kurahashi K., 1991, Biochem. Biophys. Res. Commun., 116: 751–758.
2. Gueldner R. C., Reuilly C. C., Pusey P. L. Costello E. C., Arrendale R. F., Cox R. H., Himmelsbach D. S., Crumley F. G. and Cutler H. G., 1987, J. Agric. Food Chem., 36: 366–370.
3. Arrendale R. F., Gueldner R. C., Choryk O. T. and Crumley F. G., 1988, J. Microbiol. Methods 8, 249–257.
4. Peypoux F., Besson F., Michel G. and Delcambe L., 1981, Eur. J. Biochem., 118: 323–327.
5. Kajimura Y., Sugiyama M. and Kaneda M., 1995, J. Antibiot., 48(10): 1095–103.
6. Besson F. and Michel G., 1990, Microbios, 62: 93–99.
7. Kluge B., Vater ,J., Salnikow J. and Eckart K., 1988, FEBS Letter, 231: 107.
8. Vanittanakom N, Loeffer W, 1986, J. Antibiot. 39: 888–901.
9. Tsuge K., Ano T. and Shoda M., 1996, Arch. Microbiol., 165: 243–251.
10. Klich M. A., Arthur K. S., Lax A. R. and Bland J. M., 1994,127: 123–127. French patent No. 2,644,038; 1990.
11. Landy M., Warren G. H., Rosenman S. R. and Colio L. G., 1948, Proc. Soc. Exp. Biol. Med., 67: 539–541.
12. Peypoux F., Besson F. and Michel G. Lenzen C. Dierickx L. and Delcambe L., 1980, J. Antibiot., 33(10): 1146–9
13. Mhammedi A., Peypoux F., Besson F. and Michel G., 1982, J. Antibiot., 35(3): 306–11.
14. Besson F., Peypoux F., Michel G. et Delcambe L., 1977, Eur. J. Biochem., 77(1): 61–7.
15. Eshita S. M., Roberto N. H., Beale J. M., Mayima B. M. and Workman R. F., 1995, J. Antibiot., 48(11): 1240–7.
16. Mhammedi A., Peypoux F., Besson F. and Michel G., 1981, J. Antibiot., 35(3): 306–11.
17. Tenoux I., Besson F. and Michel G., 1991, Microbios. 67: 187–193.
18. Besson F., Peypoux F. and Michel G., 1978, FEBS Letters, 90 (1): 36–40
19. Besson F., Peypoux F. and Michel G., 1979, Biochimica et Biophysica Acta, 552: 558–62.
20. Besson F., Peypoux F., Michel G. and Delcambe L., 1979, J. Antibiot., 32(8); 828–33.
21. Peypoux F., Pommier M. T., Das B., Besson F., Delcambe L. and Michel G., 1984, J. Antibiot., 37(12): 1600–4.
22. Backman et al., U.S. Pat. No. 5,888,501; 1999.
23. U.S. Pat. No. 5,888,501, Induced systemic resistance of plants to pathogenic microorganisms.
24. U.S. Pat. No. 5,294,422, Method for the Control of Prevention of Aflatoxin Contamination using a non-toxigenic strain of Aspergillus Flavus.
25. Aflatoxin in Corn, J. A. Wrather, University of Missouri Delta Center, 1998.
26. Aflatoxin, J. F. Shanahan, W. M. Brown, Jr. Colorodo State University, 1998.

We claim:

1. An isolated antifungal *Bacillus subtilis* PTA-1767 peptide selected from the group consisting of a1 and a2, and having antifungal activity against *Aspergillus flavus*, wherein said peptide is a cyclic peptide comprising a β-amino fatty acid.
2. The peptide of claim 1 further having antifungal activity against *Alternaria solani, Fusarium monoliforme* and *Pythium aphanidermatum*.
3. The peptide of claim 1 further having antibacterial activity against *Xanthomonas campestris*.
4. The peptide of claim 1 further having antibacterial activity against *Clavibacter michiganensis, Bacillus cereus* and *Bacillus subtilis* PTA-1767.
5. The peptide of claim 1 designated as a1, which has a molecular weight of 1045 Da.
6. The peptide of claim 1 designated as a2, which has a molecular weight of 1059.5 Da.
7. The peptide of claim 1, having an acidic pH.
8. The peptide of claim 7, which is soluble in water, lower alkanols and insoluble in polar solvents.
9. The peptide of claim 8, which is thermostable and resistant to lipase treatment.
10. A method for controlling fungi and bacterial plant pathogens by exposing a target plant to at least one of the peptides of claim 1, wherein the fungi are selected from the group consisting of *Aspergillus flavus, Alternaria solani, Fusarium monoliforme* and *Pythium aphanidermatum* and the bacteria are selected from the group consisting of *Clavibacter michiganensis, Xanthomonas campestris, B. cereus* and *B. subtilis* PTA-1767.

11. The method of claim 10 in which the controlling of the plant pathogens is performed by exposing the target plant to *B. subtilis* PTA-1767 which produces the peptides a1 and a2 effective to control *Aspergillus flavus*.

12. The peptide of claim 1 which has antifungal activity against *Aspergillus parasiticus*.

13. The peptide of claim 1 wherein said β-amino fatty acid of a1 comprises 15 carbons and said β-amino fatty acid of a2 comprises 16 carbons.

14. The peptide of claim 1 comprised in a crude extract from *Bacillus subtilis* PTA-1767.

15. The a1 peptide of claim 1, further having a molecular weight of about 1045 Da, and a single peak.

16. The a2 peptide of claim 1, further having a molecular weight of about 1059.5 Da, and has an additional $CH_2$ at a point other than the Glu residue.

17. A biologically pure culture of *Bacillus subtilis* identified as strain PTA-1767.

18. A method for controlling aflatoxin contamination in plants susceptible to aflatoxin-producing fungi comprising treating a plant with peptides a1 and/or a2 from *Bacillus subtilis* PTA-1767.

19. The method of claim 18, wherein the fungi is *Aspergillus flavus*.

20. A composition effective to control *Aspergillus flavus* which comprises in a mixture, an acceptable carrier and at least one active component selected from the group consisting of *B. subtilis* PTA-1767 and extracts thereof wherein said active component comprises at least one of peptides a1 and a2.

21. The composition of claim 20 wherein said peptide a1 has a molecular weight of 1045 Da and said peptide a2 has a molecular weight of 1059.5 Da.

22. The composition of claim 20 wherein said active component is peptides a1 and/or a2.

23. A method for protecting a plant from pathogens comprising contacting a target plant susceptible to an aflatoxin-generating pathogen with the composition of claim 20.

24. A treated plant which is susceptible to an aflatoxin-generating pathogen wherein the plant is treated with the composition of claim 20.

25. The treated plant of claim 24 wherein said plant is selected from the group consisting of cereals, legumes, tubers, solanaccous plants, curcurbits, and fibrous plants.

26. The treated plant of claim 24 wherein said plant is a peanut plant.

27. The treated plant of claim 26 wherein said plant is a cotton plant.

28. The treated plant of claim 26 wherein said plant is a corn plant.

29. The treated plant of claim 26 wherein said plant is a soybean plant.

* * * * *